United States Patent

Klein et al.

[11] Patent Number: 4,584,369
[45] Date of Patent: Apr. 22, 1986

[54] ANTI-LEUKEMIC BETA-GLYCOSYL C-NUCLEOSIDES

[75] Inventors: Robert S. Klein, Rye; Muill Lim, Port Chester; Wuyun Ren, New Rochelle, all of N.Y.; Joseph H. Burchenal, Noroton, Conn.

[73] Assignee: Sloan-Kettering Institute for Cancer Research, New York, N.Y.

[21] Appl. No.: 595,637

[22] Filed: Apr. 2, 1984

Related U.S. Application Data

[63] Continuation of Ser. No. 288,848, Jul. 31, 1981, abandoned.

[51] Int. Cl.⁴ .................... C08G 18/08; C08G 18/20
[52] U.S. Cl. .................................. 536/54; 536/55
[58] Field of Search .............................. 536/54, 55

[56] References Cited

U.S. PATENT DOCUMENTS 4,266,048  5/1981  Horwitz et al. ................ 536/28
4,352,795  10/1982  Cook ............................. 536/24

OTHER PUBLICATIONS

Lim et al., Tetrahedron Letters, 22 (1), pp. 25–28 (1981).
Townsend et al., J. Org. Chem., vol. 39 (14), pp. 2023–2027 (1974).

Primary Examiner—Ethel G. Love
Attorney, Agent, or Firm—Felfe & Lynch

[57] ABSTRACT

Beta-glycosyl C-nucleoside compounds showing growth inhibitory activity against leukemic cells, of the following formula, are provided:

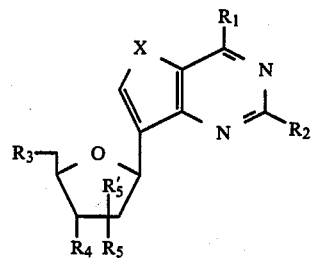

wherein
X is $NR_{10}$, S or O
$R_{10}$ is H or alkyl with 1 to 6 carbon atoms.

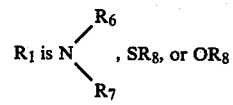

wherein $R_6$, $R_7$ and $R_8$ are independently selected from H or alkyl of 1 to 6 carbon atoms; or

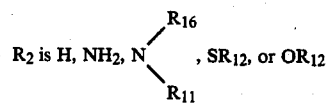

wherein $R_{16}$, $R_{11}$ and $R_{12}$ are independently selected from H or alkyl of 1–6 carbon atoms;
$R_3$ is OH, $SR_{13}$, or $OR_9$;
$R_4$ is OH, $SR_{14}$, or $OR_{15}$;
$R_9$, $R_{13}$, $R_{14}$ and $R_{15}$ are individually selected from $C_1$–$C_6$ alkyl and $C_1$ to $C_6$ acyl;
$R_5$ is OH or H,
$R'_5$ is OH or H with the provison that at least one of $R_5$ or $R'_5$ is H; excluding 2-deazoxoformycin; and HCl salts thereof.

19 Claims, No Drawings

ANTI-LEUKEMIC BETA-GLYCOSYL C-NUCLEOSIDES

The invention described herein was made in the course of work under a grant or award from the Department of Health, Education, and Welfare.

This application is a continuation of Ser. No. 288,848 filed July 31, 1981 (now abandoned).

BACKGROUND

This invention relates to an anti-cancer agent and process for preparing for same. More particularly, this invention relates to beta-glycosyl C-Nucleoside compounds which have been found to inhibit the growth of leukemic cells. The compounds have been demonstrated to have anti-tumor activity and appear to have some anti-viral activity.

Methods for making N-Nucleosides similar to the C-Nucleosides, which are the subject of this invention, are well known and well practiced. These techniques basically involve fusing an appropriate sugar to an appropriate base to form the required compound. These techniques cannot be applied to C-Nucleosides because of the low reactivity of the carbon site when compared with the nitrogen site.

To form C-Nucleosides, it has been found convenient to start with an appropriately substituted sugar moiety and "build" the desired base. However, known schemes for accomplishing this are difficult to follow and have only limited applicability because of the reagents used (see for example Gupta et al Abstract No. 40, 175 A.C.S. National Meeting, Anaheim, Calif., Mar. 13–17, 1978). Another procedure was also applied to the synthesis of a closely related compound to the inventive compounds. in Lim et al, Tetrahedron Letters, Volumn 21, pp 1013–1016 (1980). However, this compound has been found to have essentially no antitumor activity. For comparison, this compound is included in Table 1 showing relative inhibition activity for various inventive compounds (X—NH, $R_1$=OH).

SUMMARY

The present invention provides compounds having antitumor activity and which are useful in inhibiting leukemic cells.

The compounds are "built" by forming the base on a blocked sugar beta-ribofuranosyl C-Glycoside substituted by beta-dimethylaminoacrylonitrile. This starting material can be prepared by following the method of Silvano De Bernardo and Manfred Weigele, *J. Org. Chem.* Vol. 42, No. 1, pp 109–112 ) (1977). The reaction proceeds first by hydrolyzing the dimethylamino group to a hydroxyl group under conditions which do not effect the blocking groups; forming a five-membered heterocyclic ring; separating alpha and beta isomers; and forming a pyrimidine ring fused with the five-membered ring, from the beta isomer. This sugar is then unblocked, usually with hydrochloric acid, to form the compound or its corresponding hydrochloric acid salt.

TABLE 1

IN VITRO ACTIVITY ($ID_{50}$'S IN μG/ML) OF C—NUCLEOSIDES IN MOUSE AND HUMAN LEUKYMIC CELL LINES

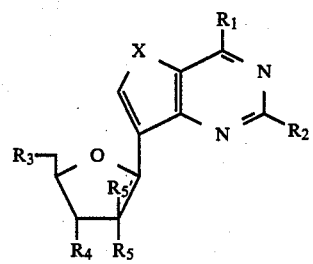

| | | P-815 | L-1210 | RAJI | ALL-CCRF-CEM | HL-60 |
|---|---|---|---|---|---|---|
| X = NH, $R_2$ = H | $R_1$ — OH, $R_2$ = H | >10(0%) | >100 | >100 | >100 | >100 |
| $R_3$ = $R_4$ = $R_5$ = OH, $R_5'$ = H | $R_1$ = SH, $R_2$ = H | 5.6 | — | — | — | — |
| | $R_1$ = SMe, $R_2$ = H | 0.3 | — | — | — | — |
| | $R_1$ = $NH_2$, $R_2$ = H | 0.001 | 0.0008 | 0.002 | 0.0008 | 0.0003 |
| X = S, $R_2$ = H | $R_1$ = OH, $R_2$ = H | 2.5 | 3.3 | 4.2 | 0.9 | 0.4 |
| $R_3$ = $R_4$ = $R_5$ = OH, $R_5'$ = H | $R_1$ = SH, $R_2$ = H | 0.5 | 0.6 | 0.9 | 1.6 | 0.4 |
| | $R_1$ = SMe, $R_2$ = H | 0.03 | 0.07 | 0.03 | 0.006 | 0.008 |
| | $R_1$ = $NH_2$, $R_2$ = H | 0.0003 | 0.0006 | 0.002 | 0.0005 | 0.0005 |

TABLE 2
IN VIVO ACTIVITY OF C—NUCLEOSIDES IN MICE

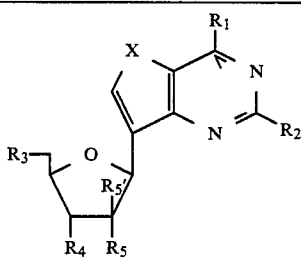

| C—NUCLEOSIDE | LINE | SCHEDULE @ DOSE (MG/KG) | % ILS |
|---|---|---|---|
| X = NH | L-1210/0 | QD × 5,$D_1$ @ 0.5 | 9.1 |
| $R_1$ = $NH_2$, $R_2$ = H | L-1210/0 | Q4D × 3,$D_1$ @ 0.25 | 17.0 |
| $R_3$ = $R_4$ = $R_5$ = OH | L-1210/MP | Q4D × 3,$D_1$ @ 0.4 | 71.8 |
| $R_5'$ = H | P-815/ARA C | Q4D × 3,$D_1$ @ 0.7 | 30.8 |
|  | P-815/ARA C | Q4D × 3,$D_1$ @ 0.4 | 19.8 |
| X = S | P-815/0 | QD × 2/Q2D × 3 @ 60 | 71.4 |
| $R_1$ = $SCH_3$, $R_2$ = H | P-815/0 | Q4D × 4,$D_1$ @ 40 | 56.3 |
| $R_3$ = $R_4$ = $R_5$ = OH |  |  |  |
| $R_5'$ = H |  |  |  |

DESCRIPTION

The beta-glycosl C-nucleoside compounds of the present invention have been shown to have anti-leukemic activity using usual techniques of the art. The results of these tests are summarized in Table 1. In addition, in vivo antitumor activity has been shown as summarized in Table 2. It is noted that the first compound in Table 1 is the compound reported in Lim et al (supra). This compound shows a lack of activity. Similar tests were also run on certain alpha-glycosyl nucleosides analogous to the inventive beta-glycosyl compounds, however these were found to be without activity.

The following preparative examples illustrate the presently preferred method of synthesizing the compounds of the present invention. (By lower alkyls is meant straight or branched alkyls of up to 6 carbon atoms).

PREPARATIVE EXAMPLE FOR PYRROLO[3,2-d]PYRIMIDINE ADENOSINE ANALOG

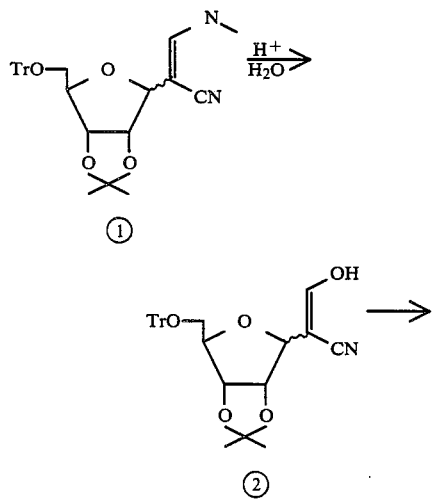

-continued

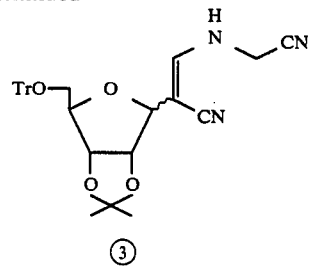

2-(2',3'-O-Isopropylidene-5'-O-Trityl-D-ribofuranosyl)-3-(N-Cyanomethylene)-aminoacrylonitrile ③

To a solution of 36 g (70 mmol.) of dimethylamino acrylonitrile ① in chloroform (720 ml) was added a solution of trifluoroacetic acid (18 ml) in water (1.2 l.) The mixture was stirred vigorously for 16 hours at room temperature and the organic layer was washed thoroughly with water and dried over anhydrous sodium sulfate filtered and evaporated to dryness in vacuo to afford 2-formylacetonitrile ②.

Without purification, ② was dissolved in methanol (420 ml) and to this was added anhydrous sodium acetate (8.6 g, 105 mmol.), aminoacetonitrile hydrochloride (8.6 g, 93 mmol.) and water (15 ml). The clear solution was stirred for 20 hours at 25° C. The solution was then diluted with chloroform (1 liter) and the mixture was poured into ice (300 g). The organic layer was separated, washed several times with water, dried over sodium sulfate and evaporated to dryness. This afforded a white solid to which was added diethyl ether. After chilling in an ice-bath the white solid was collected by suction filtration to give 30 g (81.5%) of 2-(2',3'-O-Isopropylideue-5'-O-Trityl-D-ribofuranosyl)-3-(N-cyanomethylene)-amino acrylonitrile ③ as an alpha, beta anomeric mixture. The structure was confirmed by CHN elemental analysis and NMR.

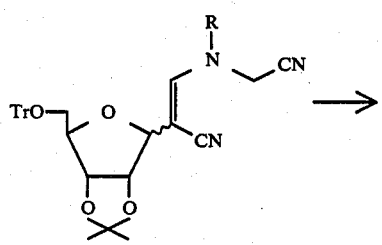

③ R = H
④ R = COOEt

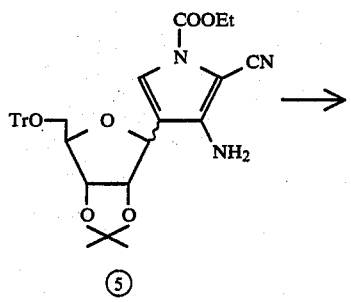

⑤

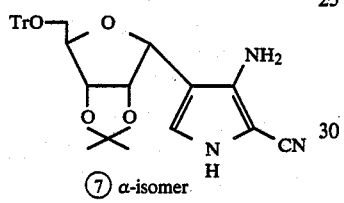

⑦ α-isomer

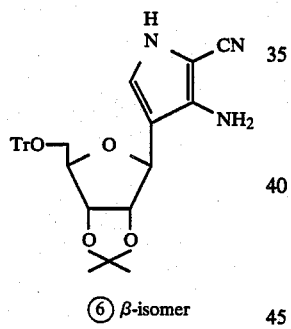

⑥ β-isomer

4-(2,3-O-Isopropylidene-5-O-Trityl-β-(and α-) D-ribofuranosyl)-2-cyano-3-aminopyrrole ⑥

To a solution of compound ③ (10.43 g, 20 mmol.) in dichloromethane (100 ml) at 0° C. was added DBN (1,5-diazabicyclo[4,3,0]non-5-ene) (4.96 g, 40 mmol.) followed by a solution of ethyl chloroformate (3.42 g, 32 mmol.) in dichloromethane (20 ml). After completion of the transformation to the N-carboethoxy derivative 4 (approximately 1 hour), an additional equivalent of DBN (2.48 g, 20 mmol.) was added and the reaction mixture was stirred at 25° C. for 20 hours and evaporated to dryness. Chromatographic purification of the residue on silica gel (chloroform/ethyl acetate; 9/1) afforded the N-carboethoxy pyrrole ⑤ (α, β-anomeric mixture) as a white foam (10 g, 84% from ③). The structure was confirmed by CHN elemental analysis and NMR spectroscopy.

Intermediate 5 (10 g, 16.8 mmol.) was dissolved in methanol (60 ml) to which was added sodium carbonate (178 mg, 1.7 mmol.). The mixture was stirred at room temperature for 50 minutes and filtered. The filtrate was evaporated and the residue was purified by flash chromatography on silica gel (toluene/ethyl acetate; 8/1) to give 5.40 g (61% from ⑤) of the desired beta-isomer ⑥ and 2.26 g (26% from ⑤) of the alpha-isomer ⑦.

Beta-isomer ⑥: MP. 170°-172° C. (Ethyl acetate/diethyl ether). Structure was confirmed by C,H,N elemental analysis and NMR spectra.

Alpha-isomer ⑦: MP. 176° C. (dec) (Acetone/Hexanes) structure was confirmed by C,H,N elemental analysis and NMR spectra.

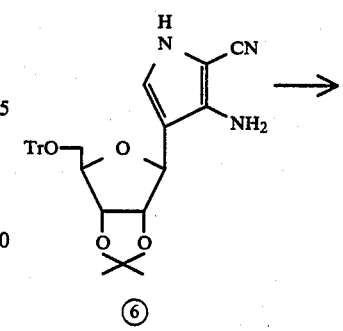

⑥

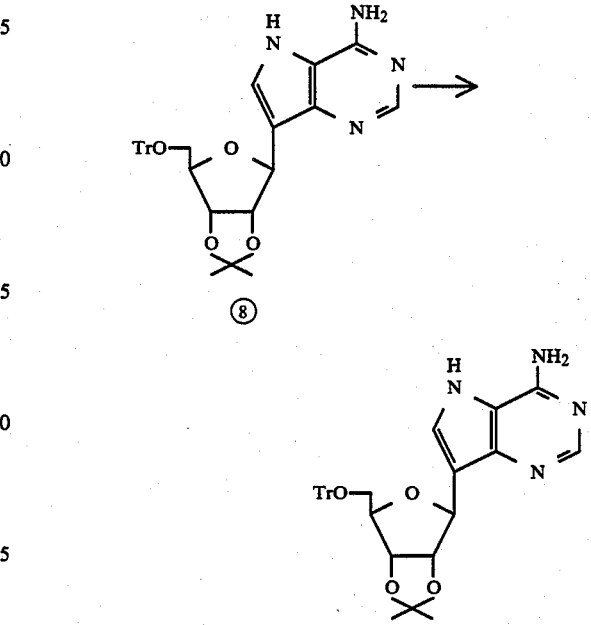

"9-Deazaadenosine"

⑨

7-(β-D-Ribofuranosyl)-4-amino-pyrrolo[3,2-d]pyrimidine 9

A mixture of the beta-3-amino-4-cyanopyrrole ⑥ (3.15 g, 6 mmol.) in absolute ethanol (25 ml) was heated to reflux for 4½ hours and evaporated to dryness in vacuo. The residue was dissolved in ethyl acetate and the solution was washed with water then brine and finally evaporated to dryness. Chromatographic purification of crude ⑧ on silica gel (dichloromethane/methanol; 20/1 then 10/1) afforded pure ⑧ as a white solid (3.1 g, 93.6%). Structure was confirmed by C,H,N element mass spectroscopy NMR and UV spectroscopy.

To a solution of the blocked C-nucleoside ⑧ (653 mg, 1.2 mmol.) in methanol (5.5 ml) was added 7.2 ml of a 12.6% solution of hydrogen chloride in methanol. The reaction mixture was stored at 20° C. for 2 hours then treated with diethylether (1-2 ml) and cooled in an ice bath. The resulting crystalline precipitate was collected by filtration to give "9-deazaadenosine" hydrochloride ⑨ (300 mg, 74%).

Recrystallization from ethanol afforded an analytically pure sample (mp: 179°-183° C.).

Analysis calculated for: C:43.63; H:4.99; N:18.49; Cl:11.72. Found: C:43.68; H:4.97; N:18.43; Cl:11.75. Structure was further confirmed by NMR and UV spectroscopy.

This procedure is applicable, inter alia to 7-(β-D-Ribofuranosyl)-2,4-diamino-pyrrolo[3,2-d]pyrimidine by substitution of guanidine carbonate for formamidine acetate in step ⑥→⑧.

7-(β-D-Ribofuranosyl)-4-amino-5-methyl (or lower alkyls)-pyrrolo[3,2-d]pyrimidine by substitution of N-Methyl (or lower alkyl) aminoacetonitrile.

By utilization of the general procedure (J. Am. Chem. Soc, 1981 (103 pp. 932–933)) for conversion of ribonucleosides to 2'-deoxynucleosides the following
7-(2'-Deoxy-β-D-ribofuranosyl)-4-amino-pyrrolo[3,2-d]pyrimidine.
7-(2'-Deoxy-β-D-ribofuranosyl)-2,4-diamino-pyrrolo[3,2-d]pyrimidine.
7-(2'-Deoxy-β-D-ribofuranosyl)-4-amino-5-methyl (or lower alkyls)-pyrrolo[3,2-d]pyrimidine.

PREPARATIVE EXAMPLE FOR THIENO[3,2-d]-(AND FURO[3,2-d])PYRIMIDINE ADENOSINE ANALOGS

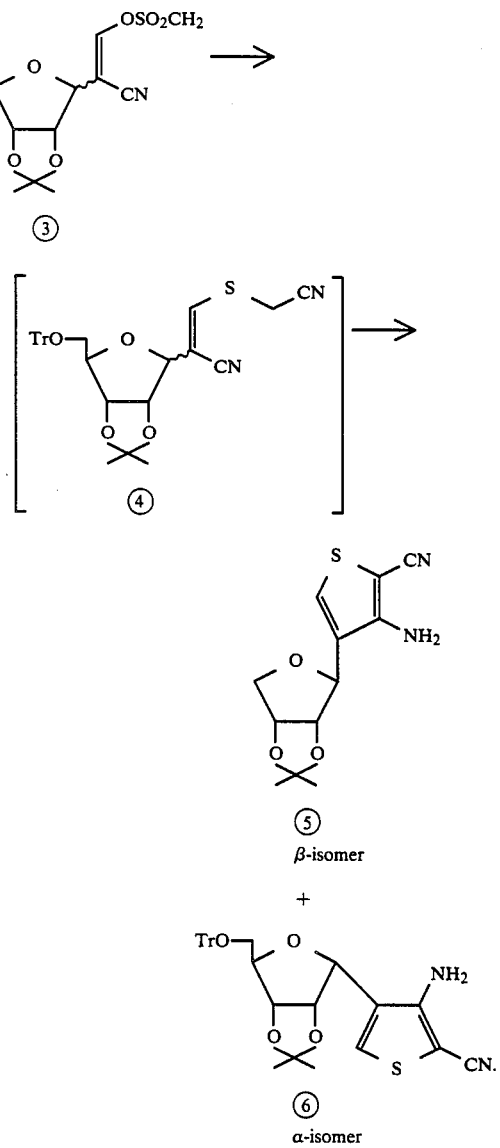

3-Methanesulfonyloxy-2-(2'3'-O-isopropylidene-5'-O-trityl-D-ribofuranosyl)-acrylonitrile Hydrolysis of 24 gm (47 mmol) of dimethylamino acrylonitrile ① as described previously afforded the corresponding crude 2-formyl acetontrile derivative ②. Without purification ② was dissolved in 160 ml of chloroform containing 8.30 ml of triethylamine and treated dropwise with a solution of 4.22 ml (54 mmol.) of methanesulfonyl chloride in 160 ml of chloroform at 0° C. with efficient stirring. After one hour, at 0° C. the reaction mixture was diluted to 500 ml with chloroform and washed well with brine. The organic layer was dried over sodium sulfate and evaporated to dryness to give a crude anomeric mixture of 3 obtained as a foam (22 gm). Purification and separation by chromatography of a small sample afforded pure anomers which were readily identified by NMR spectroscopy. The crude material was of satisfactory purity to be utilized directly in the following step.

4-(2',3'-O-Isopropylidene-5'-O-trityl-β-(and α-) D-ribofuranosyl)-3-amino-2-cyanothiophene ⑤ and ⑥

To a solution of intermediate ③ (20 g, obtained from the previous step) in 430 ml of absolute ethanol was added acetylthioacetonitrile (8 g, 70 mmol.) and anhydrous sodium carbonate (8 g, 70 mmole.). The reaction mixture was heated to reflux under N₂ for ⑦ hours and evaporated to dryness in vacuo. The residue was partitioned between chloroform and water (300 ml each) and the organic layer washed again with water. The chloroform solution was then dried over anhydrous sodium sulfate and evaporated to dryness in vacuo. The residue containing the α-β-anomeric mixture of ⑤ and ⑥ was purified by column chromatography on silica gel (Toluene) to give 5.6 gm (24.5% from ① in the previous step) of the 3-amino-2-cyanothiophene β-C-nucleoside ⑤ and 2.5 gm (11% from ① of the corresponding α-C-nucleoside ⑥. Both were obtained as syrup. Their structure was confirmed by elemental analysis and NMR spectroscopy.

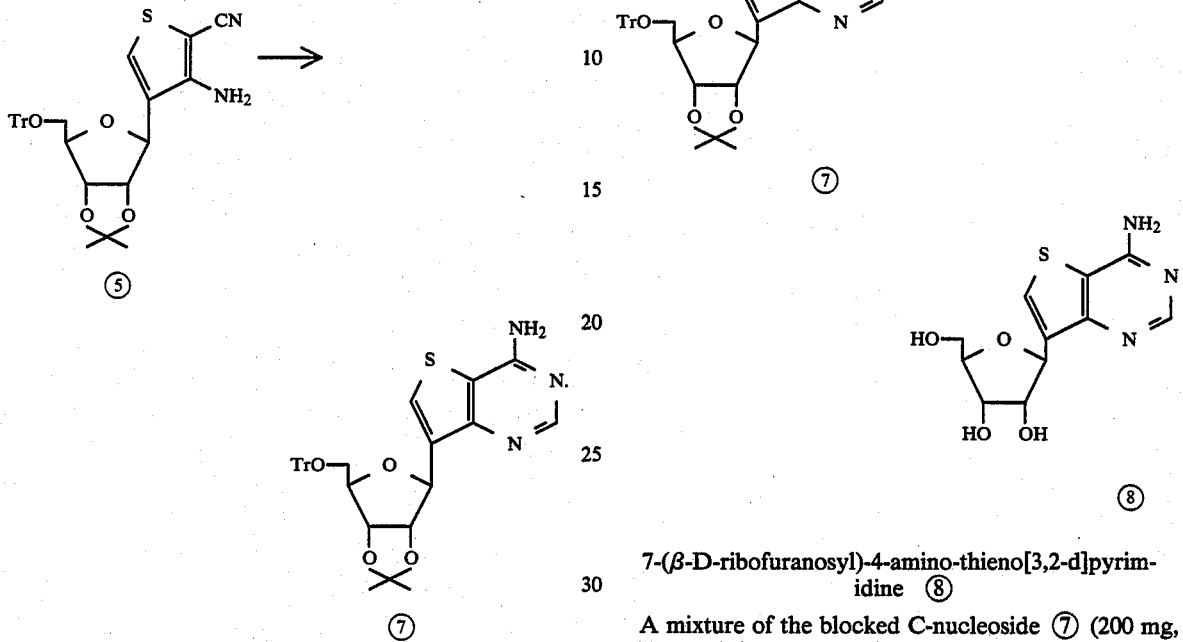

7-(2',3'-O-Isopropylidene-5'-trityl-β-D-ribofuranosyl)-4-amino-thieno[3,2-d]pyrimidine ⑦

A solution of ⑤ (1.2 gm, 2.2 mmol.) in 30 ml of absolute ethanol was heated to reflux and to this was added in several portions 7 gm of formamidine acetate (67 mmol.) over a period of 7 days. The solvent was then removed in vacuo and the residue extracted with chloroform. The chloroform solution was then washed with water, dried over anhydrous sodium sulfate and evaporated to dryness. The crude material containing 7 was purified by column chromatography on silica gel (chloroformmethanol: 20/1) to give the blocked thieno[3,3-d]pyrimidine ⑦ (1.01 gm, 80% from ⑤) as a foam. The structure was confirmed by elemental analysis and NMR spectroscopy.

7-(β-D-ribofuranosyl)-4-amino-thieno[3,2-d]pyrimidine ⑧

A mixture of the blocked C-nucleoside ⑦ (200 mg, 0.35 mmole.) and 4 ml of a 12% solution of hydrogen chloride in methanol was stirred at room temperature for 10 minutes. Diethylether (15 ml) was then gradually added to precipitate ⑧ as an amorphous solid which slowly crystallizes. Filtration and washing with diethylether finally affords 98 mg (85%) of ⑧ as a dihydrochloride salt m.p. 154°–155° C.

Elemental Analysis Calculated for: C:37.08; H:4.24; N:11.79; S:8.99; Cl:19.90. Found: C:37.74; H:4.17; 11.89; S:9.30; Cl:20.40. The structure was also confirmed by NMR spectroscopy.

The furo[3,2-d]pyrimidine compounds are prepared in an analogous manner, as shown by the following reaction scheme when compared with this preparative example.

SEQUENCE FOR THE ADENOSINE ANALOG

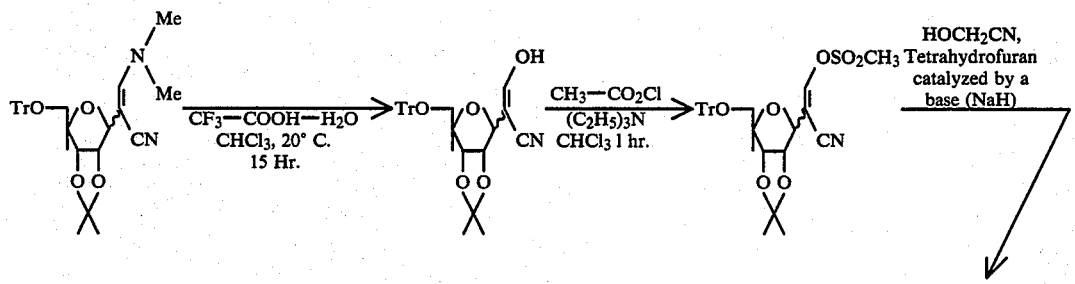

-continued
SEQUENCE FOR THE ADENOSINE ANALOG

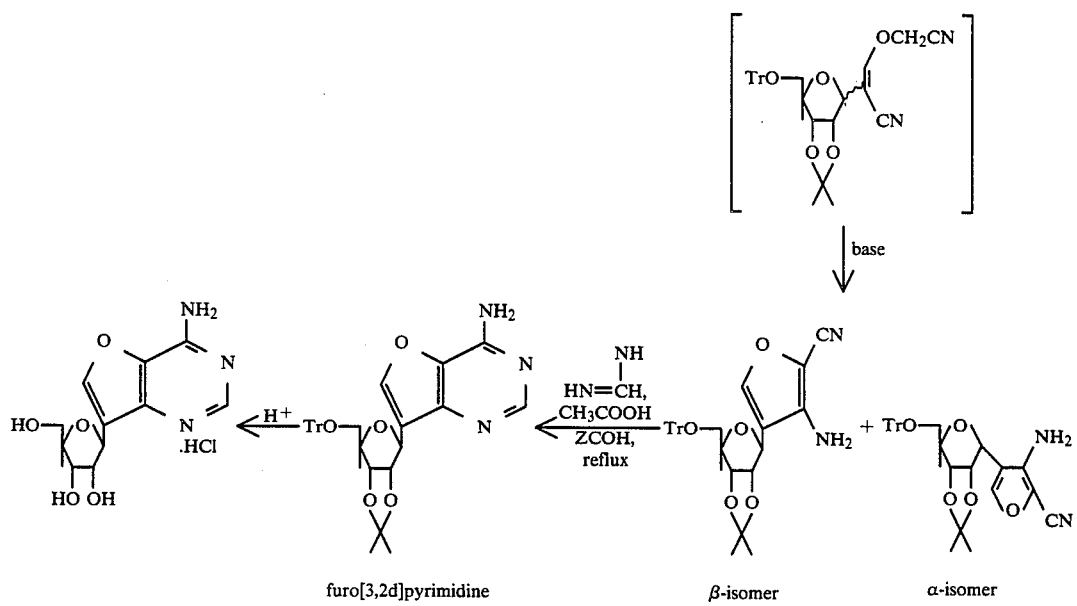

This procedure is applicable inter alia to
7-(β-D-Ribofuranosyl)-2,4-diamino-thieno[3,2-d]pyrimidine and
7-(β-D-Ribofuranosyl)-2,4-diamino-furo[3,2-d]pyrimidine by substitution of guanidine carbonate for formamidine acetate.

By utilization of the general procedure [J. Am. Chem. Soc., 1981 (103 pp 932–933)] for conversion of ribonucleosides to 2'-deoxynucleosides the following
7-(2'-Deoxy-β-D-ribofuranosyl)-4-amino-thieno[3,2-d]pyrimidine
7-(2'-Deoxy-β-D-ribofuranosyl)-4-amino-furo[3,2-d]pyrimidine
7-(2'-Deoxy-β-D-ribofuranosyl)-2,4-diamino-thieno[3,2-d]pyrimidine
7-(2'-Deoxy-β-D-ribofuranosyl)-2,4-diamino-furo[3,2-d]pyrimidine PREPARATION OF THIENO[3,2-d]PYRIMIDINE NUCLEOSIDE DERIVATIVES

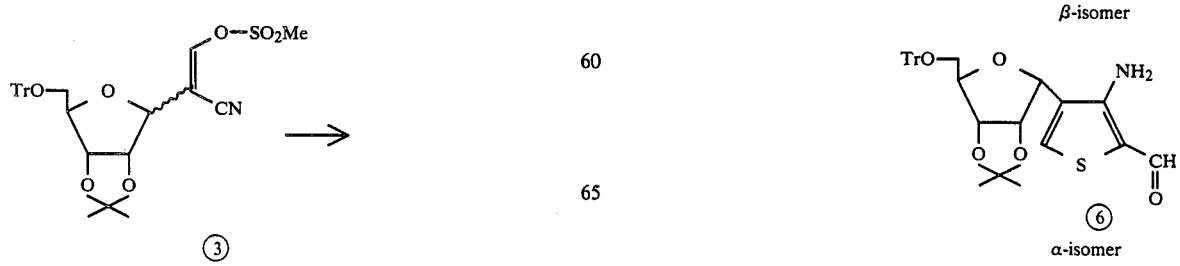

4-(2',3'-O-Isopropylidene-5'-O-trityl-β-(and α-) D-ribofuranosyl)-3-amino-2-carboxamido-thiophene. ⑤ and ⑥

To a suspension of 3-mesyloxy acetonitrile ③ (6 gm, 10.7 mmol, prepared by the method above described) in 180 ml of absolute ethanol was added mercaptoacetamide (1.5 g, 16.4 mmol) and anhydrous sodium carbonate (1.7 gm, 16.03 mmol). The reaction mixture was heated to reflux with stirring for 18 hours under a nitrogen atmosphere, allowed to cool to room temperature and filtered. The filtrate was evaporated to dryness in vacuo and the residue containing the isomers ⑤ and ⑥ chromatographed on a column of silica gel with toluene-ethyl acetate (20:1). This separation afforded pure 3-amino-2-carboxamido-β-isomer ⑤ as a foam (2.62 gm, 40% from ③) and the pure α-isomer ⑥ also as a foam (2.94 gm, 45% from ③). The structure of each was confirmed by elemental analysis and NMR spectroscopy.

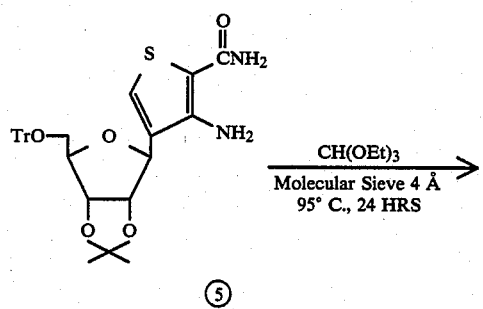

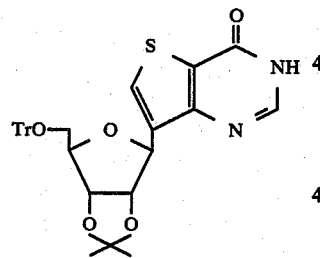

7-(2',3'-O-isopropylidene-5'-O-trityl-β-D-ribofuranosyl)-3H-4-oxo-thieno[3,2-d]pyrimidine. ⑦

To a suspension of 3-amino-2-carboxamido-thiophene ⑤ (3.5 gm, 6.29 mmol) in 20 ml of triethylorthoformate was added 1 gm of finely ground molecular sieve (4 Å). The reaction mixture was heated at 95° C. and stirred for 24 hours. After cooling to room temperature, it was filtered and to the clear filtrate was added 10 ml of petroleum ether (40°–60° C.) to precipitate compound ⑦ as a solid. This was collected by filtration, pressed into a cake, washed with petroleum ether and dried in vacuo. This procedure afforded ⑦ (2 gm, 56%) as a white powder mp 128°–130° C.

The structure was confirmed by elemental analysis and by NMR spectroscopy.

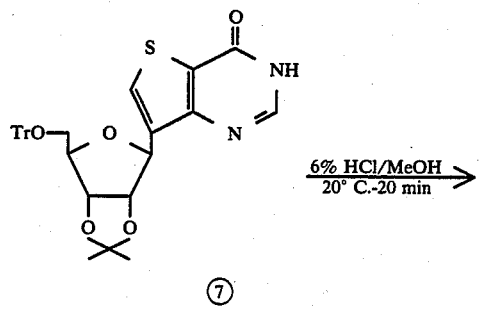

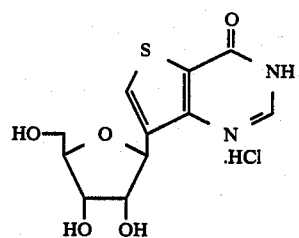

Thieno[3,2-d]pyrimidine analog of inosine.

7-(β-D-Ribofuranosyl)-3H-4-oxo-thieno[3,2-d]pyrimidine monohydrochloride ⑧

A mixture of compound ⑦ (5.8 gm, 10.24 mmol) in 50 ml of a 6% solution of hydrogen chloride in methanol was stirred at 20° C. for 20 minutes and 120 ml of diethyl ether was then added to gradually form a white precipitate. After one hour, the crystalline C-nucleoside monohydrochloride ⑧ was filtered and washed with ether to give 2.56 gm (88%) of the desired product, mp 211°–214° C.

Anal. Calcd: C: 41.19, H:4.08, N:8.73, S:9.99; Found: C:41.59, H:4.10, N:8.65, S:9.85.

Structure was confirmed by NMR spectroscopy

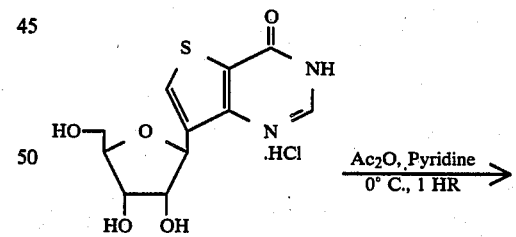

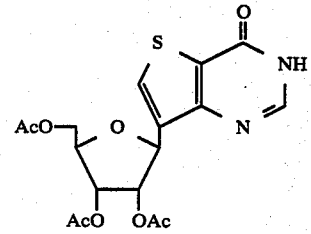

7-(2',3',5'-tri-O-acetyl-β-D-ribofuranosyl)-3H-4-oxo-thieno[3,2-d]pyrimidine ⑨

To a solution of compound ⑧ (1.5 gm, 5.28 mmol) in anhydrous pyridine (5 ml) was added acetic anhydride (5 ml) at 0° C. After one hour the mixture was partitioned between chloroform (100 ml) and water (100 ml). The organic layer was washed with water (100 ml), dried over anhydrous Na₂SO₄ and evaporated to dryness in vacuo. The residue containing ⑨ was purified by chromatography on a silica gel column with chloroform-methanol (40:1) to give 1.61 gm (75%) of the triacetate ⑨ as a colorless syrup. The structure was confirmed by elemental analysis and NMR spectroscopy.

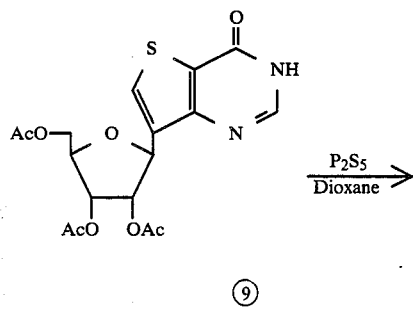

⑨

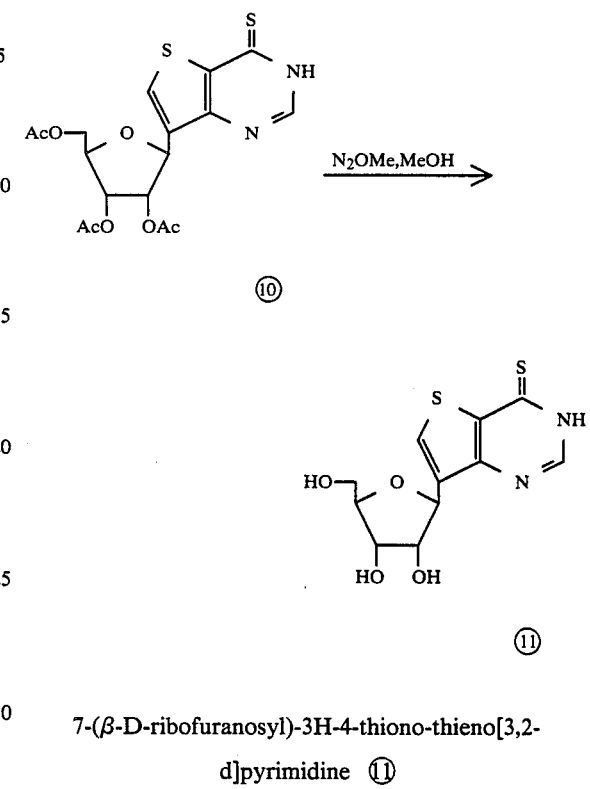

⑩
Thieno[3,2-d]pyrimidine
analog of Thioinosine

⑪

7-(2',3',5'-Tri-O-acetyl-β-D-ribofuranosyl)-3H-4-thiono-thieno[3,2-d]pyrimidine ⑩

To a solution of ⑨ (3 gm, 7.31 mmol) in 40 ml of dry dioxane heated to reflux was added 3 gm of phosphorous pentasulfide in portions (200 mg each) over a period of 1.5 hours. Heating was continued until thin layer chromatography (chloroform/methanol: 10/1) indicated that the reaction was completed. The solvent was removed in vacuo and the residue containing ⑩ was purified by chromatography on a column of silica gel (chloroform/methanol: 20/1) to give the thieno-pyrimidine thione ⑩ in pure form (2.62 gm, 84%) as a foam.

The structure was confirmed by NMR spectroscopy.

7-(β-D-ribofuranosyl)-3H-4-thiono-thieno[3,2-d]pyrimidine ⑪

A solution of triacetate ⑩ (2.02 gm, 4.74 mmol) in 40 ml of 0.1N sodium methoxide in methanol was stirred at 20° C. for 1 hour. The final solution was neutralized with IRC-50 (H⁺) ion exchange resin, filtered, and the filtrate evaporated to dryness in vacuo. The residue was dissolved in water and the aqueous solution washed with chloroform. The aqueous layer was lyophilized to give 1.36 gm (95%) of pure 7-(β-D-ribofuranosyl)-3H-4-thiono-thieno[3,2-d]pyrimidine as a powder.

The structure was confirmed by NMR spectroscopy.

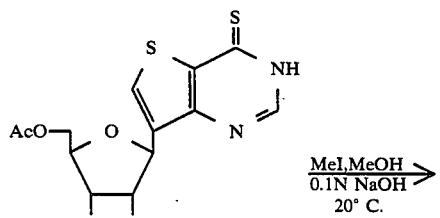

⑩

-continued

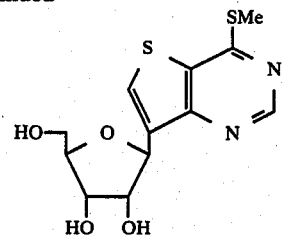

Thieno[3,2-d]pyrimidine analog of Methylthio purine riboside (12)

7-(β-D-Ribofuranosyl)-4-methylthio-thieno[3,2-d]pyrimidine (12)

To a solution of triacetate (10) (350 mg, 0.82 mmol) in a mixture of 3 ml of methanol and 3.3 ml of methyl iodide was added 10 ml of O.I.N. aqueous sodium hydroxide and the reaction mixture was stirred at room temperature for one hour. During this period, the product desired (12) precipitated. This was collected by filtration, washed with methanol then chloroform to afford 255 mg (98%) of 7-(β-D-ribofuranosyl)-4-methylthio-thieno[3,2-d]pyrimidine as a crystalline (white needles) material. One recrystallization from boiling methanol afforded the analytical sample: mp 226°–228° C.

Anal. Calcd. for C: 45.84, H: 4.48, N: 8.90, S: 20.39; Found: C: 45.89, H: 4.51, N: 8.88, S: 20.25.

The structure was confirmed by NMR spectroscopy.

What is claimed is:

1. Beta-glycosyl C-nucleoside compound of the formula

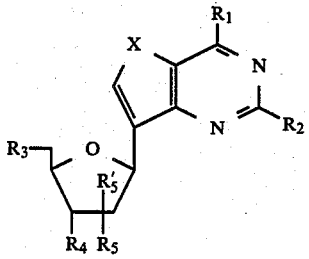

wherein
X is $NR_{10}$ or S
$R_{10}$ is H or alkyl with 1 to 6 carbon atoms,

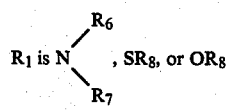

wherein $R_6$, $R_7$ and $R_8$ are independently selected from H or alkyl of 1 to 6 carbon atoms;
$R_2$ is H,
$R_3$ is OH,
$R_4$ is OH,
$R_5$ is OH or H,
$R'_5$ is OH or H with the provision that at least one of $R_5$ or $R'_5$ is H; excluding 2-deazoxoformycin; and HCl salts thereof.

2. The compound of claim 1 wherein
$X = NR_{10}$ and
$R_{10} = H$.
3. The compound of claim 2 wherein $R_1$ is OH.
4. The compound of claim 1 wherein $X = S$.
5. The compound of claim 1, 2 or 4 wherein $R_1$ is $N_2$, $NHCH_3$, SH, or $SCH_3$.
6. The compound of claim 1 wherein
$X = N$
$R_3 = R_4 = OH$
$R_5 = R'_5 = H$
$R_{10}$ is H.
7. The compound of claim 1 wherein
$X = S$
$R_3 = R_5 = OH$
$R_5 = R'_5 = H$.
8. The compound of claim 6, or 7 wherein $R_1 = NH_2$ or $NHCH_3$.
9. The compound of claim 1 designated 7-(β-D-Ribofuranosyl)-2,4-diamino-thieno[3,2-d]pyrimidine.
10. The compound of claim 1 designated 7-(2'Deoxy-β-D-ribofuranosyl)-4-amino-thieno[3,2-d]pyrimidine.
11. The compound of claim 1 designated 7-(2'-Deoxy-β-D-ribofuranosyl)-2,4-diamino-thieno[3,2-d]pyrimidine.
12. The compound of claim 1 designated 7-(2'-Deoxy-β-D-Ribofuranosyl)-4-amino-pyrrolo[3,2-d]pyrimidine.
13. The compound of claim 1 designated 7-(2'-Deoxy-β-D-Ribofuranosyl)-2,4-amino-pyrrolo[3,2-d]pyrimidine.
14. The compound of claim 1 designated 7-(β-D-Ribofuranosyl)-4-amino-5-alkylpyrrol pyrimidine wherein the alkyl is a lower alkyl group.
15. The compound of claim 1 selected from
7-(β-D-Ribofuranosyl)-4 alkyl aminopyrrolo pyrimidine,
7-(β-D-Ribofuranosyl)-4 mercapto-pyrrolo pyrimidine,
7-(β-D-Ribofuranosyl)-4 methylthio-pyrrolo pyrimidine,
7-(β-D-Ribofuranosyl)-2-amino-4-mercaptopyrrolo pyrimdine,
7-(β-D-Ribofuranosyl)-4 alkyl aminothieno pyrimidine,
7-(β-D-Ribofuranosyl)-4-mercapto-thieno pyrimidine,
7-(β-D-Ribofuranosyl)-4 alkyl thiothieno pyrimidine,
7-(β-D-Ribofuranosyl)-4-oxo-3H,5H-thieno pyrimidine (Tautomeric form of the 4 hydroxy derivative)
7-(β-D-Ribofuranosyl)-2-amino-4-oxo-3H,5H-thieno pyrimidine (Tautomeric form),
7-(β-D-Ribofuranosyl)-2-amino-4-mercapto-thieno pyrimidine,
7-(2'-Deoxy-β-D-Ribofuranosyl)-4-methylalkyl-thieno pyrimidine,
7-(2'-Deoxy-β-D-Ribofuranosyl)-4-oxo-3H,5H-thieno pyrimidine (Tautomeric form of the 4 hydroxy derivative)
7-(2'-Deoxy-β-D-Ribofuranosyl)-2-amino-4-oxo-3H,5H-thieno pyrimidine (Tautomeric form), 7-(2'-Deoxy-β-D-Ribofuranosyl)-4-methylalkylpyrrolo pyrimidine, wherein the alkyls are individually selected from lower alkyl groups.

16. Beta-glycosyl C-nucleoside compound of the formula

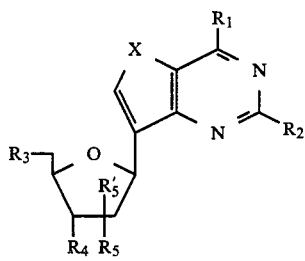

wherein

X is $NR_{10}$, S $R_{10}$ is H or alkyl with 1 to 6 carbon atoms,

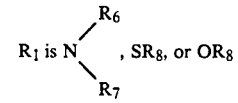

wherein $R_6$, $R_7$ and $R_8$ are independently selected from H or alkyl of 1 to 6 carbon atoms;

$R_2$ is H;

$R_3$ is OH, $R_4$ is OH, $R_5$ is OH, $R'_5$ is H excluding 2-deazoxoformycin; and HCl salts thereof.

17. The compound of claim 16 designated 7-(β-D-Ribofuranosyl)-4-amino-pyrrolo[3,2d]pyrimidine.

18. The compound of claim 16 designated 7-(β-D-Ribofuranosyl)-4-amino-5 alkyl-pyrrolo[3,2-d]pyrimidine wherein the alkyl is a lower alkyl group.

19. The compound of claim 16 designated 7-(β-D-Ribofuranosyl)-4-amino-thieno [3,2-d]pyrimidine.

* * * * *